United States Patent [19]

Yoshida et al.

[11] Patent Number: 5,107,039

[45] Date of Patent: Apr. 21, 1992

[54] OPTICALLY ACTIVE CYCLOPENTENOLS AND PROCESS FOR PREPARING THE SAME

[75] Inventors: Naoyuki Yoshida; Kazutoshi Miyazawa, both of Ichihara, Japan

[73] Assignee: Chisso Corporation, Osaka, Japan

[21] Appl. No.: 567,013

[22] Filed: Aug. 13, 1990

[30] Foreign Application Priority Data

Aug. 25, 1989 [JP] Japan .................................. 1-218884

[51] Int. Cl.⁵ ........................ C07C 35/06; C07C 69/02
[52] U.S. Cl. .................................. 568/838; 560/231; 554/229
[58] Field of Search ................ 568/838, 700; 260/410; 560/231

[56] References Cited

U.S. PATENT DOCUMENTS 3,344,191 9/1967 Chappell ............................ 568/838

FOREIGN PATENT DOCUMENTS

A1-9892 4/1980 European Pat. Off. ............ 568/838
A1-3724721 4/1989 Fed. Rep. of Germany ...... 568/838

OTHER PUBLICATIONS

Gasson et al., "J. Chem. Soc." pp. 2798-2800 (1950).
English et al., "J. Amer. Chem. Soc." vol. 74 pp. 1909-12 QDI.A5.
Wiemann et al., "Chemical Abstract" vol. 37, p. 1933 1957.
Brown et al., "Chem. & Eng. News" pp. 36-37 (Jan. 19, 1959).
Huckel et al., "Ann. der Chemie", vol. 649, pp. 13-20 (Nov. 1961).

*Primary Examiner*—Werren B. Lone
*Attorney, Agent, or Firm*—Wenderoth, Lind & Ponack

[57] ABSTRACT

Optically active cyclopentenols are here disclosed which are represented by the formula (I)

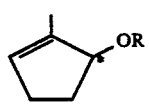

(I)

(wherein R is a hydrogen atom or an acyl group having 2 to 15 carbon atoms, and the sign * denotes a chiral carbon atom).

The optically active cyclopentenols can be prepared by a process which comprises the step of carrying out a transesterification between (±)-cyclopentenol represented by the formula (IV)

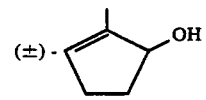

(IV)

and triglyceride or vinyl ester by the use of esterase to obtain an optically active cyclopentenol represented by the formula (II)

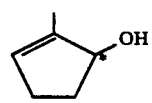

(II)

and an optically active cyclopentenol derivative represented by the formula (III)

(III)

(wherein R' is an acyl group having 2 to 15 carbon atoms, and the sign * denotes a chiral carbon atom) which is a derivative of the enantiomer of the cyclopentenol (II); or alternatively, by another process which comprises the step of hydrolysis or alcoholysis of an optically active cyclopentenol derivative represented by the formula (III)

(III)

(wherein R' is an acyl group having 2 to 15 carbon atoms, and the sign * denotes a chiral carbon atom) to obtain an optically active cyclopentenol represented by the formula (II)

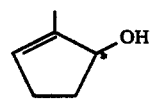

(II)

having the same absolute configuration as in the aforesaid derivative.

3 Claims, No Drawings

OPTICALLY ACTIVE CYCLOPENTENOLS AND PROCESS FOR PREPARING THE SAME

BACKGROUND OF THE INVENTION (i) Field of the Invention

The present invention relates to an optically active cyclopentenol and its derivative as well as a process for preparing the same.

(ii) Description of Related Art

An optically active cyclopentenol has a fundamental structure which is utilized to synthesize the basic skeleton of a physiologically active natural material such as a steroid or an alkaloid, and the above kind of cyclopentenol is considered to be useful for the asymmetric synthesis. However, there is not known a synthesis technique for the optically active cyclopentenol, much less an industrially excellent and efficient synthetic process.

Taking such situation into consideration, the present inventors have researched intensively so as to obtain both the enantiomers of an optically active cyclopentenol and its derivative, and as a result, the present invention has been achieved.

SUMMARY OF THE INVENTION

An object of the present invention is to provide an optically active cyclopentenol.

Another object of the present invention is to provide an optically active cyclopentenol derivative.

Still another object of the present invention is to provide an effective process for preparing an optically active cyclopentenol and its derivative (hereinafter abbreviated to cyclopentenols).

According to an aspect of the present invention, there are provided optically active cyclopentenols represented by the formula (I)

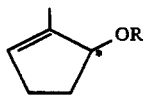
(I)

(wherein R is a hydrogen atom or an acyl group having 2 to 15 carbon atoms, and the symbol * denotes a chiral carbon atom).

According to another aspect of the present invention, there is provided a process for preparing the optically active cyclopentenols which comprises the step of carrying out a transesterification between (±)-cyclopentenol represented by the formula (IV)

(IV)

and triglyceride or a vinyl ester of a fatty acid (hereinafter abbreviated to vinyl ester) by the use of esterase to obtain an optically active cyclopentenol represented by the formula (II)

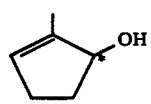
(II)

and an optically active cyclopentenol derivative represented by the formula (III)

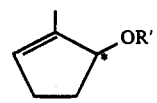
(III)

(wherein R' is an acyl group having 2 to 15 carbon atoms, and the symbol * denotes a chiral carbon atom) which is a derivative of the enantiomer of the above-mentioned cyclopentenol (II).

According to still another aspect of the present invention, there is provided a process for preparing the optically active cyclopentenols which comprises the step of hydrolysis or alcoholisis of an optically active cyclopentenol derivative represented by the formula (III)

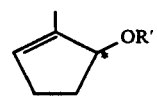
(III)

(wherein R' is an acyl group having 2 to 15 carbon atoms, and the symbol denotes a chiral carbon atom) in order to obtain an optically active cyclopentenol represented by the formula (II)

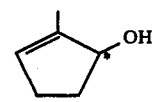
(II)

having the same absolute configuration as in the aforesaid derivative.

DESCRIPTION OF THE PREFERRED EMBODIMENTS

The optically active cyclopentenols of the present invention are represented by the formula (I)

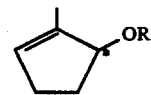
(I)

(wherein R is a hydrogen atom or an acyl group having 2 to 15 carbon atoms, and the symbol * denotes a chiral carbon atom).

More specifically, the present invention is directed to an optically active cyclopentenol represented by the formula (II)

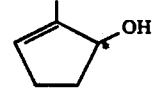
(II)

and an optically active cyclopentenol derivative represented by the formula (III)

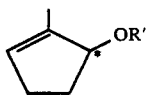

(III)

(wherein R' is an acyl group having 2 to 15 carbon atoms, and the symbol * denotes a chiral carbon atom).

A first process for preparing the optically active cyclopentenols of the present invention comprises the step of carrying out a transesterification between (±)-cyclopentenol represented by the formula (IV)

(IV)

and triglyceride or vinyl ester by the use of esterase to obtain an optically active cyclopentenol represented by the formula (II)

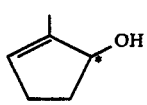

(II)

and an optically active cyclopentenol derivative represented by the formula (III)

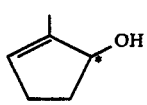

(III)

(wherein R' is an acyl group having 2 to 15 carbon atoms, and the symbol * denotes a chiral carbon atom) which is a derivative of the enantiomer of the above-mentioned cyclopentenol (II).

A second process for preparing the optically active cyclopentenols of the present invention comprises the step of hydrolysis or alcoholysis of an optically active cyclopentenol derivative represented by the formula (III)

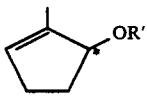

(III)

(wherein R' is an acyl group having 2 to 15 carbon atoms, and the symbol * denotes a chiral carbon atom) to obtain an optically active cyclopentenol represented by the formula (II)

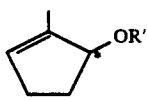

(II)

having the same absolute configuration as in the aforesaid derivative.

Typical compounds of the optically active cyclopentenol represented by the formula (II) of the present invention include S-(−)-2-methyl-2-cyclopentenol represented by the formula (II')

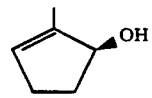

(II')

and R-(+)-2-methyl-2-cyclopentenol represented by the formula (II'')

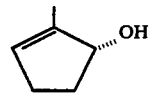

(II'')

Detailed examples of the optically active cyclopentenol represented by the formula (III) of the present invention are S-(−)-cyclopentenol derivatives represented by the formula

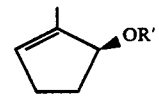

and R-(+)-cyclopentenol derivatives represented by the formula

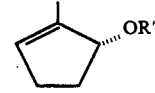

Typical examples of these optically active cyclopentenol derivatives include S-(−)-1-acetyloxy-2-methyl-2-cyclopentene represented by the formula

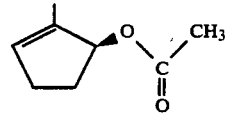

R-(+)-1-acetyloxy-2-methyl-2-cyclopentene represented by the formula

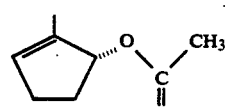

S-(−)-1-propanoyloxy-2-methyl-2-cyclopentene,
R-(+)-1-propanoyloxy-2-methyl-2-cyclopentene,
S-(−)-1-butyryloxy-2-methyl-2-cyclopentene,
R-(+)-1-butyryloxy-2-methyl-2-cyclopentene,
S-(−)-1-caproyloxy-2-methyl-2-cyclopentene, R-(+)-1)-caproyloxy-2-methyl-2-cyclopentene,
S-(−)-1-lauryloxy-2-methyl-2-cyclopentene and
R-(+)-1-lauryloxy-2-methyl-2-cyclopentene.

The first process of the present invention is based on a transesterification reaction represented by the following reaction formula:

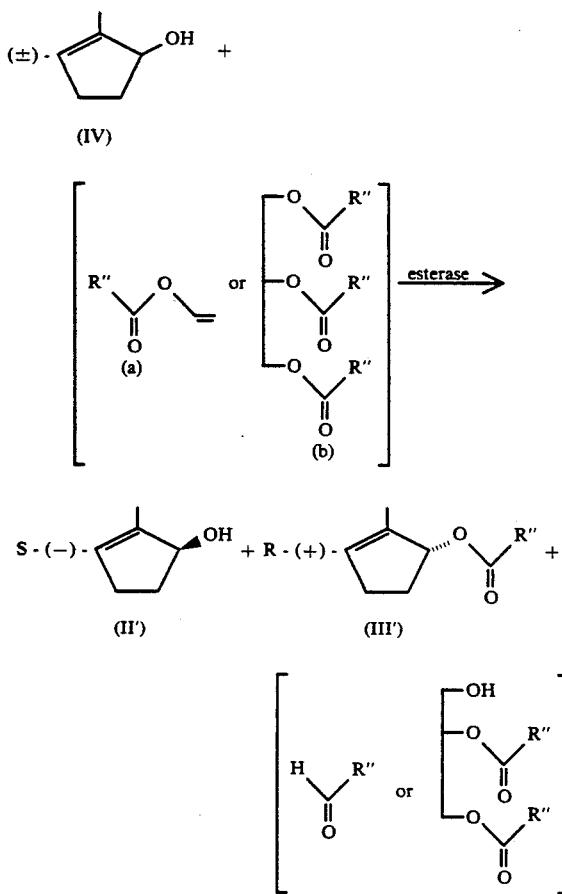

(wherein R" is an alkyl group having 1 to 14 carbon atoms).

The reaction is carried out by mixing (±)-2-methyl-2-cyclopentenol [formula (IV)]with about 0.5 equivalent of vinyl ester [formula (a)]or triglyceride [formula (b)], and then efficiently bringing the mixture into contact with esterase in order to obtain S-(−)-cyclo-pentenol [formula (II')]and R-(+)-cyclopentenol derivative [formula (III')].

Furthermore, the sign of a specific rotation, (+)-or (−)-, depends upon the kind of esterase which is used in the reaction. That is, examples having these signs are R-(−)-cyclopentenol and an S-(+)-cyclopentenol derivative represented by the following formulae (II") and (III"), respectively:

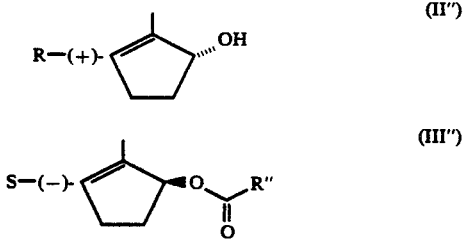

With regard to reaction conditions for the first process of the present invention, a suitable reaction temperature is from room temperature (about 10° C.) to 150° C., preferably from 20° to 45° C. A reaction time depends upon (±)-2-methyl-2-cyclopentenol as a substrate, and vinyl ester or triglyceride as an acylating agent, but it is usually from 1 to 1,000 hours. Furthermore, a ratio of (±)-2-methyl-2-cyclopentenol to the acylating agent is from 1:0.01 to 1:1.5 (molar ratio), preferably 1:0.5 (molar ratio).

After the transesterification reaction, an esterase powder can be collected by a usual filtration and then reused directly. The reaction solution which is the resulting filtrate can be separated into optically active 2-methyl-2-cyclopentenol and optically active 1-acyloxy-2methyl -2-cyclopentene by means of reduced pressure distillation or column chromatography. After completion of the reaction, if 2-methyl-2-cyclopentenol (which is the remaining cyclopentenol) which has not been acylated has a low optical purity (if the transesterification does not proceed sufficiently), the transesterification reaction can be carried out again by the use of esterase, thereby obtaining a product having a high optical purity.

(±)-2-Methyl-2-cyclopentenol represented by the formula (II) which is the starting material in the first manufacturing process of the present invention can be obtained by reducing 2-methyl-2-cyclopentenone (formula c) with sodium borohydride in the presence of cerous chloride:

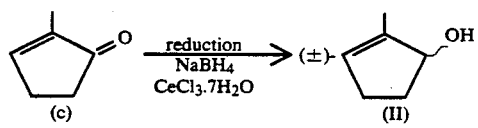

In the present invention, various reaction solvents can be used, so long as they do not impair an esterase activity, and examples of the reaction solvent include hydrocarbons such as n-hexane and n-heptane, benzene, toluene and ethers.

Examples of the triglyceride regarding the present invention include triacetin, tripropionin, tributyrin, tricaproin and trilaurin.

Examples of the vinyl ester regarding the present invention include vinyl acetate, vinyl propionate, vinyl butyrate, vinyl caproate and vinyl laurate.

As esterase regarding the present invention, enzymes can be used which are produced by microorganisms and which are derived from animals. Examples of commercially available esterase are as follows:

TABLE

| Trade Name | Origin | Seller or Maker |
| --- | --- | --- |
| Lipase P | Pseudomonas fluorescens | Amano Pharmaceutical Co., Ltd. |
| Lipase CES | Pseudomonas sp | Amano Pharmaceutical Co., Ltd. |
| Lipase AP | Aspergillus niger | Amano Pharmaceutical Co., Ltd. |
| Lipase M | Mucor javanicus | Amano Pharmaceutical Co., Ltd. |
| Lipase CE | Humicola lanuginosa | Amano Pharmaceutical Co., Ltd. |
| Lipase F-AP | Rhizopus javanicus | Amano Pharmaceutical Co., Ltd. |
| Lipase II | Porcine pancreas | Sigma Chemical Co. |
| Lipase VIII | Geotrichum Candidum | " |
| Lipase X | Rhizopus delamar | " |
| Lipase | Chromobacterium Viscosum | Toyo Jozo Co., Ltd. |
| Lipase A | Aspergillus niger | Novo Industi A/S |
| Lipase | Rhizopus niveus | Nagase Biochemicals, Ltd. |

In addition, esterase produced by any kind of microorganisms is usable. Examples of such microorganisms include microorganisms belonging to Pseudomonas genus, Arthrobacter genus, Acromobacter genus, Alcaligenes genus, Aspergillus genus, Chromobacterium genus, Candida genus, Mucor genus and Rhizopus genus.

Above all, the microorganisms belonging to the Pseudomonas genus are particularly preferable.

The second preparation process of the present invention comprises subjecting the optically active cyclopentenol derivative represented by the formula (III) obtained by the first manufacturing process of the present invention to an alkali hydrolysis, an acid hydrolysis or an alcoholysis so as to remove the acyl group therefrom, thereby obtaining optically active 2-methyl-2-cyclopentenol having the same absolute configuration as in the optically active cyclopentenol derivative used as the starting material, i.e., the antipode of optically active 2-methyl-2-cyclopentenol obtained by the first manufacturing process.

Examples of the base which can be used in the hydrolysis include potassium hydrogencarbonate, potassium hydroxide and sodium hydroxide; and examples of the usable acid include hydrochloric acid and sulfuric acid. In the alcoholysis, methanol and ethanol can be used.

According to the above-mentioned first and second manufacturing processes of the present invention, (+)-and (−)- type optically active 2-methyl-2-cyclopentenols can be obtained.

The optically active cyclopentenols of the present invention are very useful intermediates for an asymmetric synthesis.

Furthermore, it is fair to say that the manufacturing process of the present invention is an industrially excellent and effective synthetic process.

The optically active cyclopentenol of the present invention can increase carbon atoms by a dislocation reaction without impairing its optical purity, its steric configuration being maintained, as shown in the following:

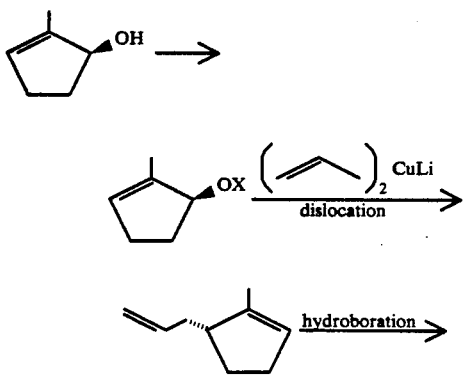

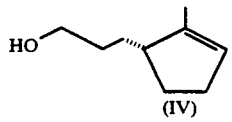

(wherein X is $CH_3CO$, $CH_3C_6H_5SO_2$, $CH_3SO_2$, and

denotes an allyl group). That is, the hydroxyl group is modified with a protective group X which will be a leaving group and is then dislocated with allyl copper lithium or allyl magnesium bromide in order to introduce the allyl group into the cyclopentenol, and a terminal olefin is then treated by hydroboration in order to lead to a compound having the skeleton of the formula (IV). The compound having the formula (IV) is useful as a fundamental skeleton (intermediate) of a physiologically active natural material such as a steroid or an alkaloid and can be applied in many fields.

Now, the present invention will be described in more detail in reference to examples, but the scope of the present invention should not be limited to these examples.

EXAMPLE 1

In a 500-ml three-necked flask, 20.29 g (0.21 mol) of 2-methyl-2-cyclopentenone was dissolved in 300 ml of methanol, and 77.6 g (0.21 mol) of cerous chloride was further dissolved in the solution, followed by stirring at room temperature for 15 minutes and ice cooling. Afterward, 7.93 g (0.21 mol) of sodium borohydride was added thereto over 40 minutes with care so as not to exceed a reaction temperature of 20° C. After completion of the reaction was confirmed by means of thin-layer chromatography, the methanol solvent was distilled off under reduced pressure, and the residue was then extracted with 1.6 liters of ether. The extract was then washed with 500 ml of a saturated aqueous sodium chloride solution and then dried with magnesium sulfate, followed by filtration. Next, ether was distilled off under reduced pressure to obtain 19.85 g of a liquid. The latter was then distilled, thereby obtaining 14.5 g (0.14 mol, yield 70%) of (±)-2-methyl-2-cyclopentenol having a boiling point of from 67° to 68° C.

3.93 g (0.04 mol) of the thus obtained (±)-2-methyl-2-cyclopentenol was mixed with 4.5 g (0.02 mol) of vinyl laurate, and 5 g of Lipase P (made by Amano Pharmaceutical Co., Ltd.) was further added thereto, followed by stirring at room temperature for 7 hours to carry out reaction. The resulting reaction solution was then filtered to remove a lipase powder therefrom, and the filtrate was concentrated under reduced pressure to obtain 7.8 g of a liquid. Next, the latter was separated into 3.4 g (0.013 mol, oily material) of (+)-1-lauryloxy-2-methyl-2-cyclopentene and 1.9 g (19 mmol, boiling point 71° to 72° C./35 mmHg) of (−)-2-methyl-2-cyclopentenol by column chromatography (eluent: toluene/ethyl acetate =10/1).

The specific rotation of (+)-1-lauryloxy-2-methyl-2-cyclopentene was $[\alpha]^{28}_D$ +35.52° (c1.57,$CHCl_3$).

The specific rotation of (−)-2-methyl-2-cyclo-pentenol was $[\alpha]^{31}_D$ −41.3° (c 1.02, $CHCl_3$).

EXAMPLE 2

3.4 g (0.013 mol) of (+)-1-lauryloxy-2-methyl-2-cyclopentene and potassium hydrogencarbonate were stirred in a dioxane/water (1/1) solvent at room temperature for 10 hours so as to carry out reaction. 500 ml of ether was then added thereto, and the solution was transferred to a separatory funnel and then shaken. Afterward, an aqueous phase was separated out, and an ether phase was washed with 300 ml of a saturated aqueous sodium chloride solution (ice cooling). The ether phase was then dried with magnesium sulfate, and the solvent was distilled off, followed by distillation, thereby obtaining (+)-2-methyl-2-cyclopentenol. The specific rotation of this compound was $[\alpha]^{29}_D + 44.1°$ (c 0.78, CHCl$_3$).

What is claimed is:

1. An optically active compound represented by the formula (I)

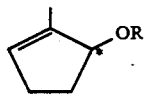

(I)

wherein R is a hydrogen atom or an acyl group having 2 to 15 carbon atoms, and the symbol * denotes a chiral carbon atom.

2. The optically active compound according to claim 1 which is an optically active cyclopentenol represented by the formula (II):

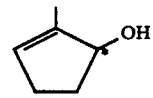

(II)

3. The optically active cyclopentenol and its derivative according to claim 1 which is an optically active cyclopentenol derivative represented by the formula (III);

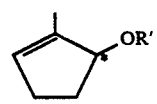

(III)

wherein R' is an acyl group having 2 to 15 carbon atoms, and the symbol * denotes a chiral carbon atom.

* * * * *